(12) United States Patent
Claridge et al.

(10) Patent No.: US 12,331,281 B2
(45) Date of Patent: Jun. 17, 2025

(54) METHOD FOR DIRECTING CELL ADHESION AND GROWTH USING ULTRATHIN STRIPED MOLECULAR FILMS

(71) Applicant: Purdue Research Foundation, West Lafayette, IN (US)

(72) Inventors: Shelley A. Claridge, Lafayette, IN (US); Tyson C. Davis, Lafayette, IN (US); Sarah Calve, West Lafayette, IN (US); Alita Miller, West Lafayette, IN (US); Anamika Singh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 900 days.

(21) Appl. No.: 17/466,048

(22) Filed: Sep. 3, 2021

(65) Prior Publication Data

US 2022/0064586 A1 Mar. 3, 2022

Related U.S. Application Data

(60) Provisional application No. 63/073,961, filed on Sep. 3, 2020.

(51) Int. Cl.
*C12N 1/04* (2006.01)
*C12M 1/00* (2006.01)
(Continued)

(52) U.S. Cl.
CPC ............... *C12N 1/04* (2013.01); *C12M 23/04* (2013.01); *C12M 23/20* (2013.01); *C12M 25/06* (2013.01);
(Continued)

(58) Field of Classification Search
CPC .... C12N 1/04; C12N 5/0068; C12N 2513/00; C12N 2533/30; C12N 2533/80;
(Continued)

(56) References Cited

U.S. PATENT DOCUMENTS

| 6,368,877 B1 * | 4/2002 | Zhang | C12N 5/0068 426/531 |
|---|---|---|---|
| 2012/0129209 A1 * | 5/2012 | Khine | C12N 5/0068 435/402 |

(Continued)

OTHER PUBLICATIONS

Plow, E. F.; Haas, T. A.; Zhang, L.; Loftus, J.; Smith, J. W., Ligand Binding to Integrins. J.Biol. Chem. 2000, 275, 21785-21788.
(Continued)

*Primary Examiner* — Michael L Hobbs
(74) *Attorney, Agent, or Firm* — Purdue Research Foundation

(57) ABSTRACT

This present disclosure relates to a designed material surface mimicking properties of an extracellular matrix or matrisome, as a means for modulating cell adhesion, spreading, proliferation, differentiation, or reprogramming; and for controllable, directional cell adhesion, spreading, proliferation, differentiation, or reprogramming. In particular, this present disclosure relates to a designed material surface mimicking properties of large polysaccharides for modulating cell adhesion, proliferation, differentiation, or reprogramming of a cell, and to materials for scaffolding cell growth. Processes and composition matters are within the scope of this patent application.

16 Claims, 13 Drawing Sheets

(51) Int. Cl.
*C12M 1/12* (2006.01)
*C12N 5/00* (2006.01)
*C08L 83/04* (2006.01)

(52) U.S. Cl.
CPC ............ *C12N 5/0068* (2013.01); *C08L 83/04* (2013.01); *C12N 2513/00* (2013.01); *C12N 2533/30* (2013.01)

(58) Field of Classification Search
CPC ...... C12M 23/04; C12M 23/20; C12M 25/06; C12M 35/04; C08L 83/04
See application file for complete search history.

(56) References Cited

U.S. PATENT DOCUMENTS

| 2015/0125952 | A1* | 5/2015 | Kim | A61L 27/3873 |
|---|---|---|---|---|
| | | | | 435/396 |
| 2018/0229265 | A1* | 8/2018 | Claridge | B05D 5/06 |

OTHER PUBLICATIONS

Stevens, M. M.; George, J. H., Exploring and Engineering the Cell Surface Interface. Science 2005, 310, 1135-1138.

Bang, J. J.; Rupp, K. K.; Russell, S. R.; Choong, S. W.; Claridge, S. A., Sitting Phases ofPolymerizable Amphiphiles for Controlled Functionalization of Layered Materials. J. Am. Chem.Soc. 2016, 138, 4448-4457.

Claridge, S. A., Standing, Lying, and Sitting: Translating Building Principles of the CellMembrane to Synthetic 2D Material Interfaces. Chem. Comm. 2018, 54, 6681-6691.

Calve, S.; Isaac, J.; Gumucio, J. P.; Mendias, C. L., Hyaluronic Acid, Has1, and Has2 AreSignificantly Upregulated During Muscle Hypertrophy. Am. J. Physiol.—Cell Physiol. 2012, 303, C577-588.

Holmes, M. W. A.; Bayliss, M. T.; Muir, H., Hyaluronic Acid in Human Articular Cartilage.Biochem. J. 1988, 250, 435-441.

Kalluri, R.; Weinberg, R. A., The Basics of Epithelial-Mesenchymal Transition. J. Clin. Invest. 2009, 119, 1420-1428.

Lutolf, M. P.; Hubbell, J. A., Synthetic Biomaterials as Instructive ExtracellulrMicroenvironments for Morphogenesis in Tissue Engineering. Nat. Biotechnol. 2005, 23, 47-55.

Han, X.; Zheng, Y.; Munro, C. J.; Ji, Y.; Braunschweig, A. B., Carbohydrate Nanotechnology: Hierarchical Assembly Using Nature's Other Information Carrying Biopolymers. Curr. Opin. Biotechnol. 2015, 34, 41-47.

Zhang, S. G.; Yan, L.; Altman, M.; Lassle, M.; Nugent, H.; Frankel, F.; Lauffenburger, D. A.; Whitesides, G. M.; Rich, A., Biological Surface Engineering: A Simple System for Cell Pattern Formation. Biomater. 1999, 20, 1213-1220.

Hovis, J. S.; Boxer, S. G., Patterning and Composition Arrays of Supported Lipid Bilayers by Microcontact Printing. Langmuir 2001, 17, 3400-3405.

Kam, L.; Shain, W.; Turner, J. N.; Bizios, R., Axonal Outgrowth of Hippocampal Neurons on Micro-Scale Networks of Polylysine-Conjugated Laminin. Biomater. 2001, 22, 1049-1054.

Okawa, Y.; Akai-Kasaya, M.; Kuwahara, Y.; Mandal, S. K.; Aono, M., Controlled Chain Polymerisation and Chemical Soldering for Single-Molecule Electronics. Nanoscale 2012, 4, 3013-3028.

Villarreal, T. A.; Russell, S. R.; Bang, J. J.; Patterson, J. K.; Claridge, S. A., Modulating Wettability of Layered Materials by Controlling Ligand Polar Headgroup Dynamics. J. Am. Chem. Soc. 2017, 139, 11973-11979.

Hayes, T. R.; Bang, J. J.; Davis, T. C.; Peterson, C. F.; McMillan, D. G.; Claridge, S. A., Multimicrometer Noncovalent Monolayer Domains on Layered Materials through Thermally Controlled Langmuir-Schaefer Conversion for Noncovalent 2D Functionalization. ACS Appl. Mater. Interf. 2017, 9, 36409-36416.

Davis, T. C.; Bang, J. J.; Brooks, J. T.; McMillan, D. G.; Claridge, S. A., Hierarchically Patterned Noncovalent Functionalization of 2D Materials by Controlled Langmuir-Schaefer Conversion. Langmuir 2018, 34, 1353-1362.

Bang, J. J.; Porter, A. G.; Davis, T. C.; Hayes, T. R.; Claridge, S. A., Spatially Controlled Noncovalent Functionalization of 2D Materials Based on Molecular Architecture Langmuir 2018, 34, 5454-5463.

Davis, T. C.; Bang, J. J.; Brooks, J. T.; McMillan, D. G.; Claridge, S. A., Hierarchical Noncovalent Functionalization of 2D Materials by Controlled Langmuir-Schaefer Conversion. Langmuir 2018, 34, 1353-1362.

\* cited by examiner

Fig. 8A
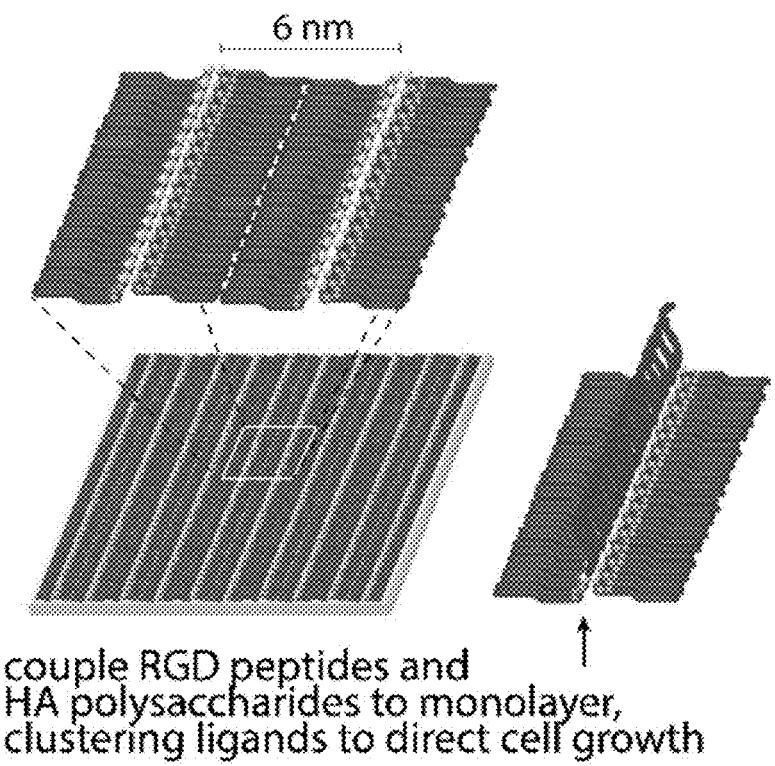
couple RGD peptides and
HA polysaccharides to monolayer,
clustering ligands to direct cell growth
arginyl-glycyl-aspartic acid
(RGD)
D-glucuronic
acid
N-acetyl-D-
glucosamine
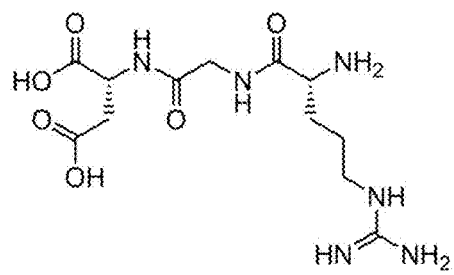
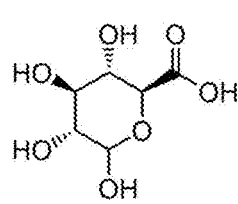
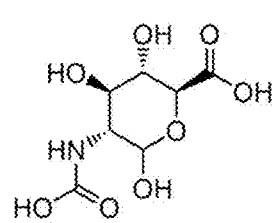
ΔDiHA
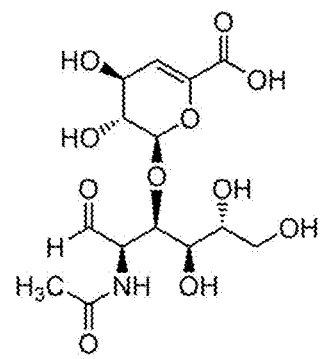
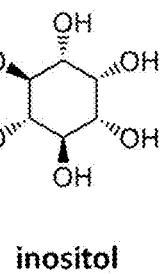
inositol
Fig. 8B

METHOD FOR DIRECTING CELL ADHESION AND GROWTH USING ULTRATHIN STRIPED MOLECULAR FILMS

CROSS-REFERENCE TO RELATED APPLICATIONS

The present U.S. patent application relates to and claims the priority benefit of U.S. Provisional Patent Application Ser. No. 63/073,961, filed Sep. 3, 2020, the contents of which are hereby incorporated by reference in its entirety into this disclosure.

TECHNICAL FIELD

The present disclosure relates to a designed material surface mimicking properties of an extracellular matrix or matrisome, as a means for modulating cell directional adhesion, spreading, proliferation, differentiation, or for inducing cellular reprogramming; and for controllable, directional cell adhesion, spreading, proliferation, or differentiation, or for cellular reprogramming. In particular, this present disclosure relates to a designed material surface mimicking properties of large polysaccharides for modulating cell adhesion, proliferation, or differentiation of a cell, or for inducing cellular reprogramming, and to materials for scaffolding cell growth.

BACKGROUND

This section introduces aspects that may help facilitate a better understanding of the disclosure. Accordingly, these statements are to be read in this light and are not to be understood as admissions about what is or is not prior art.

Cellular interactions with the extracellular matrix (ECM) are central in processes related to normal human development and function: cell migration in the embryo, tissue formation during organogenesis, and later regeneration in wound healing.[2,10-11] Interactions with the cell microenvironment are also important in the progression of human diseases, such as the epithelial-to-mesenchymal transition in cancerous tumors.[10] The ECM comprises at least three significant classes of components: (1) a base of insoluble collagen fibers that contribute mechanical stability, (2) proteoglycans (e.g. aggrecan) and large glycosaminoglycans (carbohydrates) such as hyaluronic acid (HA) which typically have high surface charge densities, leading to strong hydration that supports dynamic mechanical stability,[12] and (3) ECM proteins and other specific chemical signals that mediate interactions between cells and the structural elements of the ECM.

Given the complexity of the cellular environment, substantial efforts in areas ranging from regenerative medicine to cancer biology have been directed toward developing environments that model specific aspects of the ECM.[2] Such models provide testbeds for aspects of cell—environment interactions difficult to rigorously probe in the convoluted cellular environment. Much of the work on designing artificial ECM mimics for regenerative medicine has targeted display of ligands for integrins, a class of heterodimeric receptor proteins that bind to short, chemically specific peptide sequences in the ECM.[1] In part through results from model systems, it is known that binding efficiency of peptides (e.g. RGD) to integrins is altered based on a variety of factors that impact local chemical environment. These include flanking amino acid residues, 3D spatial display of the peptide, and the presence or absence of divalent cations.[13] Carbohydrates such as HA are also of significant importance in ECM display of proteoglycans and in more directly mediating interactions with cells. However, controlled carbohydrate display at interfaces represents a long-standing challenge.[14] Perhaps unsurprisingly, given the structural anisotropy and multilayered mechanical environment in the ECM, topographic and mechanical cues in the substrate also modulate cellular response to the ECM. Together, these factors add complexity in designing artificial ECM mimics for regenerative medicine and other applications.

BRIEF DESCRIPTION OF THE DRAWINGS

Embodiments of the present disclosure will now be described by way of example in greater detail with reference to the attached Figures, in which:

FIG. 8A depicts the precise surface functional patterns to mimic ligand clustering in cell interactions with the extracellular matrix (ECM). FIG. 8B shows the chemical structures of some examples of the functional headgroups.

FIG. 9A shows SEM striped molecular layer on HOPG; FIG. 9B shows fluorescence microscopy of striped molecular layer after transfer to PDMS; FIG. 9C shows optical microscopy after C2C12 cell growth.

FIG. 11A shows long range ordering in diyne PE template; FIG. 11B show short range ordering in diyne PE template; FIG. 11C shows ordering on PDMS.

FIG. 12A: preparing a modified amphiphile with carbohydrate headgroup similar to one of the constituents of hyaluronic acid, and an alkyl chain modified with an internal diyne; FIG. 12B: assembling the modified amphiphile on HOPG to achieve a striped phase, in which the molecules lie down on the surface, and the carbohydrate-modified headgroups are aligned over a desired distance; and FIG. 12C: photopolymerization of the striped phase to generate carbohydrate polymers with desired lengths; and optionally, covalent transfer of the amphiphilic carbohydrate polymer layer to a desired substrate (here, PDMS, which is suitable for cell culture).

DETAILED DESCRIPTION

Figure 1:
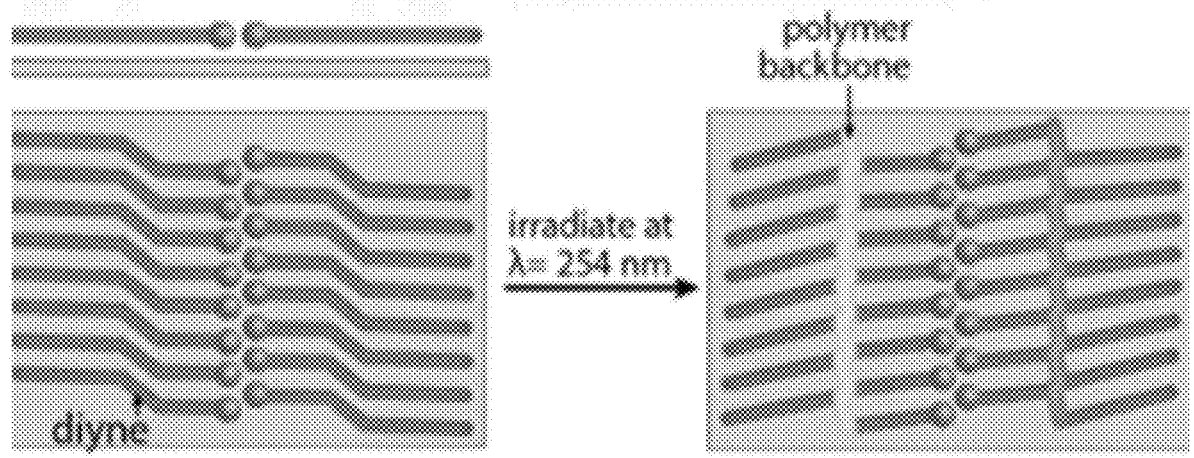
FIG. 1 illustrates assembly of ligand clusters using striped lying-down phases of polymerized diynes.
Figure 1:
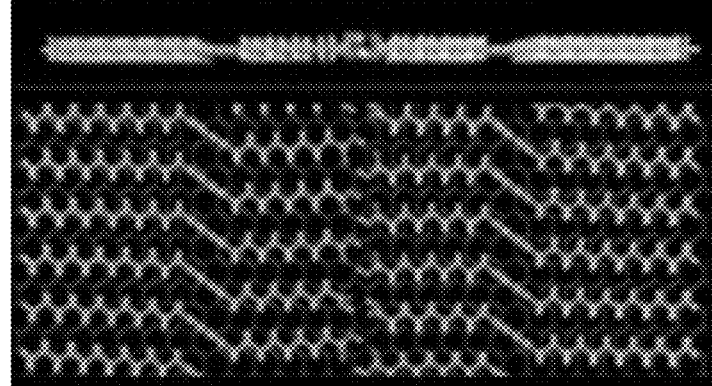
Figure 1:
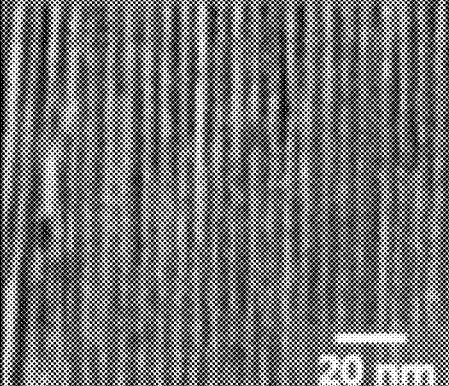
Figure 1:
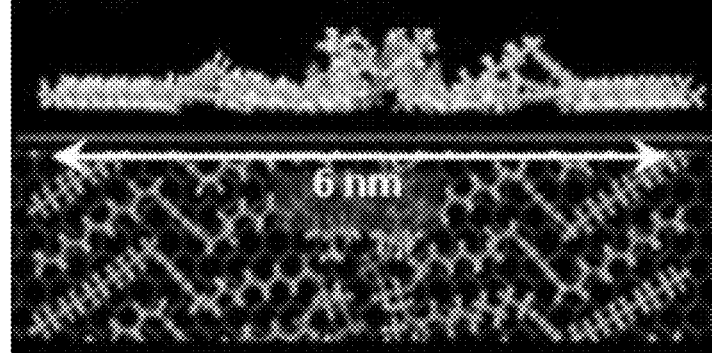
Figure 1:
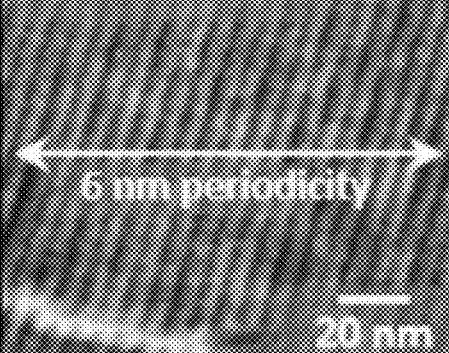

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 20%, within 10%, within 5%, or within 1% of a stated value or of a stated limit of a range.

In the present disclosure the term "substantial" or "substantially" can allow for a degree of variability in a value or range, for example, within 80%, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

As used herein, an "amphiphile" is defined as a chemical compound comprising both hydrophilic and hydrophobic constituents.

As used herein, a "monolayer" or a "thin film", used without distinctions, is defined as a layer of material ranging from less than 1 nm to several thousand nanometers in thickness.

In some illustrative embodiments, this disclosure relates to a surface-functionalized cell culture support, wherein said surface of the support material is modified by a transferred monolayer of polymerized striped phases of molecules comprising one or more chemical functional groups, one or more long alkyl chains, and one or more polymerizable functional groups; wherein said transferred striped monolayer is useful for modulating directional adhesion, proliferation, differentiation, or reprogramming of a cell.

In some illustrative embodiments, this disclosure relates to a surface-functionalized cell culture support as disclosed herein, wherein the spatially controlled arrangement of chemical functional groups of the striped phase occurs at a sub-10-nm scale for the spatial placement of those functional elements.

In some illustrative embodiments, this disclosure relates to a surface-functionalized cell culture support as disclosed herein, wherein the spatial arrangement and/or orientation and mechanical coupling of chemical functional groups in the striped phase through the polymerized striped phase polymer backbone mimics signaling and structural elements of macromolecular components of extracellular matrix or matrisome, and therefore modulates the directional adhesion, proliferation, differentiation, or reprogramming of a cell.

In some illustrative embodiments, this disclosure relates to a surface-functionalized cell culture support as disclosed herein, wherein the distinct mechanical properties of said cell culture support and said striped phase polymer backbone and/or covalent linkages between the cell culture support and the striped phase polymer backbone participate in modulating the directional adhesion, proliferation, differentiation, or reprogramming of a cell.

In some illustrative embodiments, this disclosure relates to a surface-functionalized cell culture support as disclosed herein, wherein the spatial arrangement of the chemical functional groups of the striped monolayer mimic properties of polysaccharide components of an extracellular matrix useful for modulating adhesion, proliferation, differentiation, or reprogramming of a cell.

In some illustrative embodiments, this disclosure relates to a surface-functionalized cell culture support as disclosed herein, wherein the polysaccharide is hyaluronic acid.

In some illustrative embodiments, this disclosure relates to a surface-functionalized cell culture support as disclosed herein, wherein said cell is a myoblast.

In some illustrative embodiments, this disclosure relates to a surface-functionalized cell culture support as disclosed herein, wherein the support material is polydimethylsiloxane (PDMS).

In some illustrative embodiments, this disclosure relates to a surface-functionalized cell culture support as disclosed herein, wherein said chemical functional groups comprise a carbohydrate, a peptide having the sequence of Arg-Gly-Asp or a functional analog thereof, a matrisome component, or a combination thereof.

And yet in some other illustrative embodiments, this disclosure relates to a transferred striped monolayer compatible to be added to a traditional cell culture support comprising polymerized striped phases of molecules comprising one or more chemical functional groups, one or more long alkyl chains, and one or more polymerizable functional groups, wherein said transferred striped monolayer is useful for modulating directional adhesion, proliferation, differentiation, or reprogramming of a cell.

In some other illustrative embodiments, this disclosure relates to a transferred striped monolayer compatible to be added to a traditional cell culture support comprising polymerized striped phases of molecules as disclosed herein, wherein the spatially controlled arrangement of chemical functional groups in the striped phase with elements of the spatial placement occurs at a sub-10-nm scale.

In some other illustrative embodiments, this disclosure relates to a transferred striped monolayer compatible to be added to a traditional cell culture support comprising polymerized striped phases of molecules as disclosed herein, wherein said traditional cell culture support is polydimethylsiloxane (PDMS).

In some other illustrative embodiments, this disclosure relates to a transferred striped monolayer compatible to be added to a traditional cell culture support comprising polymerized striped phases of molecules as disclosed herein, wherein the mechanical coupling of chemical functional groups in the striped phase through the polymerized striped phase polymer backbone modulates the directional adhesion, proliferation, differentiation, or reprogramming of a cell.

In some other illustrative embodiments, this disclosure relates to a transferred striped monolayer compatible to be added to a traditional cell culture support comprising polymerized striped phases of molecules as disclosed herein, wherein said cell is used for tissue engineering or repairment.

In some other illustrative embodiments, this disclosure relates to a transferred striped monolayer compatible to be added to a traditional cell culture support comprising polymerized striped phases of molecules as disclosed herein, wherein said cell is a myoblast.

In some other illustrative embodiments, this disclosure relates to a transferred striped monolayer compatible to be added to a traditional cell culture support comprising polymerized striped phases of molecules as disclosed herein, wherein the spatial arrangement and/or orientation and mechanical coupling of chemical functional groups in the striped phase through the polymerized striped phase polymer backbone mimics signaling and structural elements of macromolecular components of extracellular matrix or matrisome, and therefore modulates the directional adhesion, proliferation, differentiation, or reprogramming of a cell.

In some other illustrative embodiments, this disclosure relates to a transferred striped monolayer compatible to be added to a traditional cell culture support comprising polymerized striped phases of molecules as disclosed herein, wherein distinct mechanical properties of said cell culture support and said striped phase polymer backbone and/or covalent linkages between the cell culture support and the polymer backbone participate in modulating the directional adhesion, proliferation, differentiation, or reprogramming of a cell.

In some other illustrative embodiments, this disclosure relates to a surface or a template comprising a monolayer of a polymerized striped phase with chemical functional groups, wherein the structure of said striped phase spatially controls arrangement of said functional groups with elements of the spatial placement occurring at sub-10-nm scales, and wherein said striped monolayer mimics properties of macromolecules or components of the extracellular matrix useful for modulating the directional adhesion, proliferation, differentiation, or reprogramming of a cell.

In some other illustrative embodiments, this disclosure relates to a transferred striped monolayer compatible to be added to a traditional cell culture support comprising polymerized striped phases of molecules as disclosed herein, wherein the arrangement of the chemical functional groups of the striped monolayer mimic properties of polysaccharide components of an extracellular matrix useful for modulating adhesion, proliferation, differentiation, or reprogramming of a cell.

Yet in some additional illustrative embodiments, this is disclosure relates to a method for organizing or directing cell growth, or for tissue engineering, wherein said method utilizes a surface, a monolayer, or a template as disclosed herein.

A monolayer, or two-dimensional (2D) material generally has a layer thickness between one atomic layer and a few nm. Even though the existence of two-dimensional materials have been theorized since the 1940's (Wallace, P. R. *Phys. Rev.* 1947, 71, 622-634), it was not until 2004 that it was shown that these materials can be stable as freestanding sheets, by the isolation of individual graphene sheets (Novoselov, K. S. et al., *Science* 2004, 306, 666-669). Layers may be stacked to form macroscopic materials; for instance, highly oriented pyrolytic graphite (HOPG) consists of stacks of graphene layers.

In some illustrative embodiments, this invention relates to a relates to a designed material surface mimicking properties of an extracellular matrix or matrisome, as a means for modulating cell adhesion, spreading, proliferation, or differentiation, or for cellular reprogramming; and for controllable, directional cell adhesion, spreading, proliferation, or differentiation, or for cellular reprogramming. In particular, this present disclosure relates to a designed material surface mimicking properties of large polysaccharides for modulating cell adhesion, proliferation, or differentiation of a cell, or for inducing cellular reprogramming, and to materials for scaffolding cell growth. Processes and composition matters are within the scope of this patent application.

Molecular monolayers are often used to control the surface chemistry of materials. For instance, functional alkanethiol monolayers on coinage metals (Au, Ag, etc.) have been broadly used to change the surface chemistry of the metal surface to control its interactions with the environment. Patterned transfer of alkanethiols to the metal surface using techniques including microcontact printing enables patterning of surface chemistry at µm and 100-nm scales. Silane chemistry can similarly be used to control local functional patterning of $SiO_2$ and soft materials including poly(dimethylsiloxane) (PDMS).

Noncovalently functionalized 2D materials (e.g. graphite, graphene, $MoS_2$) are notable in regards to interfacial templating, because structural motifs in the monolayer structure enable creation of high-resolution functional patterns with scales well below 10 nm. Molecules in noncovalently adsorbed monolayers on 2D materials such as graphite typically rely in part on large van der Waals contact areas with the substrate (e.g. long alkyl chains, polycyclic aromatic hydrocarbons) to stabilize the monolayer. Due to the large area occupied by each molecule on the surface, such monolayers can present structured binding sites including 1-nm wide functional stripes (e.g. COOH, $NH_2$) with ~5-nm pitch, or 1-10 nm pores in which the substrate is exposed; such motifs allow for the adsorption of nanoscopic objects (e.g. C60, metallic nanocrystals).

The noncovalent molecule-substrate contact confers less stability than the more robust bonds (e.g. thiol-Au) that stabilize standing phase monolayers. However, assembly of molecules that incorporate a polymerizable moiety enables molecules within the monolayer to be tethered together, increasing stability. FIG. 1 illustrates noncovalent lamellar monolayers of diynoic acids and diyne phospholipids, which assemble on highly oriented pyrolytic graphite (HOPG) and other 2D materials. Photopolymerization of the diyne creates a conjugated ene-yne polymer backbone. The primary interest in this surface chemistry has been in utilization of the ene-yne as molecular wire; however, its presence can also be used to increase monolayer robustness.

Here, we describe a method for the rational design of ligand clusters, including complex functionalities such as carbohydrates, for artificial ECM scaffolds. Microcontact printing and other lithographic methods have been widely used to pattern surface chemistry[5] to mimic aspects of the cellular microenvironment,[15-17] including ligand clustering. Clustering at scales of 50-100 nm has been observed to change cell growth habits.<ref 18> However, lithographic methods are limited in terms of the smallest features that are straightforward to reproduce on a surface. Thus, impacts of clustering at smaller scales is challenging to test using surface chemical methodology available to date.

Figure 2:
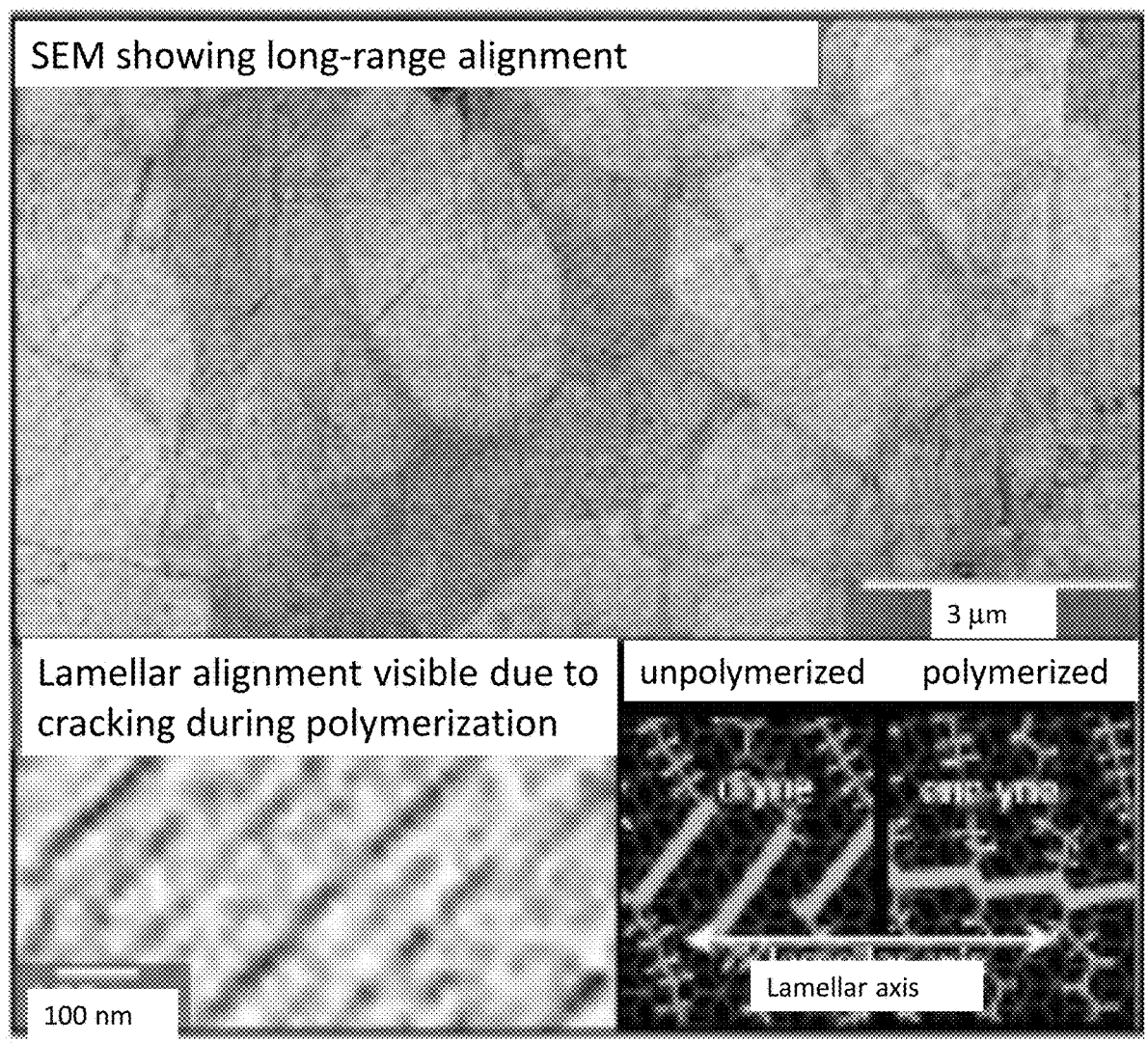
FIG. 2 shows SEM images of striped lying-down phase monolayers of polymerized diynes revealing molecular alignment through cracking during polymerization.

A different body of surface chemistry literature points to a means of examining ligand clustering at higher resolution and with greater anisotropy. Amphiphiles such as long-chain carboxylic acids (FIG. 1) can self-assemble on substrates such as highly oriented pyrolytic graphite (HOPG) with the long axis of the molecule parallel to the substrate. Ordering is driven in part by reasonably good epitaxy between the zig-zag alkyl backbone and the hexagonal graphite lattice. Lateral interactions between alkyl chains stabilize formation of striped lamellar phases.[19-20] Assembly of molecules containing an internal diyne functional group allows the monolayer to be photopolymerized with UV light[21-22]—this process can stabilize the ordering of the monolayer by tethering together molecules laterally along the row. Importantly, the monolayer structure creates nm-wide stripes of functional headgroups separated by distances from 5-10 nm; the distance between stripes is precisely tunable based on the alkyl chain length. Previously, we have demonstrated that the details of the chemical structure of the amphiphile head and tail in the striped phase can strongly impact interactions between the surface and the environment.[6,23] We have also developed unique tools and methods that enable the molecular layer structure to be controlled and characterized at scales (FIG. 2, typical cluster lengths 100 nm to 10 μm),[24-26] relevant to chemical features (e.g. large HA molecules) in the ECM.

Recently, we have also demonstrated it is possible to (a) use microcontact printing to assemble geometrically controlled microscale areas of striped phases, and (b) transfer molecular layers off of the HOPG support on which they are assembled, onto softer PDMS surfaces appropriate for cell adhesion and growth.

Here, we report a method to use the monolayers to display linear clusters of simple and complex functional components of the ECM. Our particular focus is on mimicking the structure of HA, relevant to establishing scaffolds that support regeneration of muscle and other tissues for regenerative medicine. More generally, the capability for controlled interfacial display of carbohydrates addresses a longstanding need in understanding cell-ECM interactions.

As a proof of concept, we first created striped phases of single-chain diyne amphiphiles with simple headgroup chemistries (—COOH, —NH2) and diyne phospholipids (diyne PE). Amphiphiles are assembled on HOPG using procedures reported previously by the PI's laboratory.[26,28-29] Briefly, amphiphiles are assembled on an aqueous subphase in a Langmuir trough and compressed to the desired surface pressure for transfer (e.g. 10 mN/m for diyne PE) chosen to optimize coverage or domain size during transfer. At the desired surface pressure, freshly cleaved HOPG is loaded on a custom-built thermally controlled stage designed by the PI's lab,[28] and lowered slowly into contact with the subphase. Transfer temperatures are chosen based on previous optimization (typically 50-70° C.). During contact, molecules transfer from the standing phase Langmuir film to form a striped phase on the HOPG. The HOPG is slowly withdrawn from the subphase and placed under a UV lamp for 1 hr for photopolymerization of the diyne, to increase robustness of the monolayer.

After the structure of the striped phase is stabilized, striped phases are transferred to a PDMS surface appropriate for cell growth. PDMS base and crosslinker (Sylgard 184) are premixed in a 10:1 ratio, dropcast to a typical thickness of 2-3 mm for mechanical stability, and cured for 24 h at 60° C. Following curing, removal of PDMS from the HOPG surface results in transfer of the striped phase, which remains localized on the PDMS surface through covalent linkages to the ene-yne backbone. Molecular domain morphology and molecular row orientation are characterized by fluorescence microscopy and atomic force microscopy.

To examine cell growth in relation to functional group clustering on the substrate, functionalized PDMS substrates are placed in multi-well plates to facilitate imaging of cell migration and fusion via widefield microscopy. To minimize impacts of adventitious adsorbents that may modulate adhesion and spreading, cells are cultured in Advanced DMEM, enabling serum-free culture for the times proposed. Cells are plated at a subconfluent density to enable the relationship between spreading and surface ligand clustering to be established.

Figure 7:
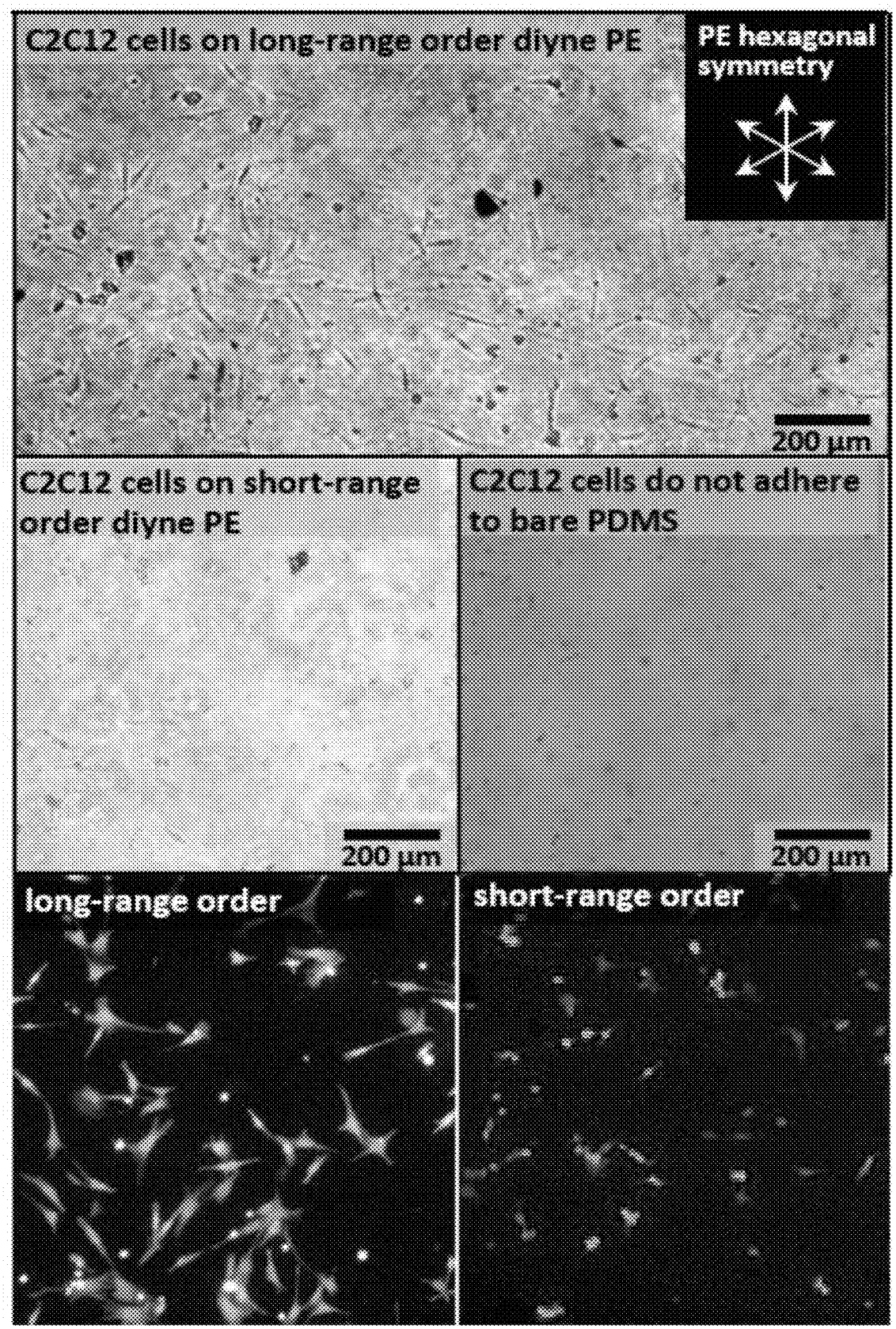
FIG. 7. Murine myoblast C2C12 cells plated on diyne PE on PDMS that exhibits long-range ordering (top) and short-range ordering (middle). Bottom two images enhance contrast from the fluorescence channels in above images.
Figure 9A:
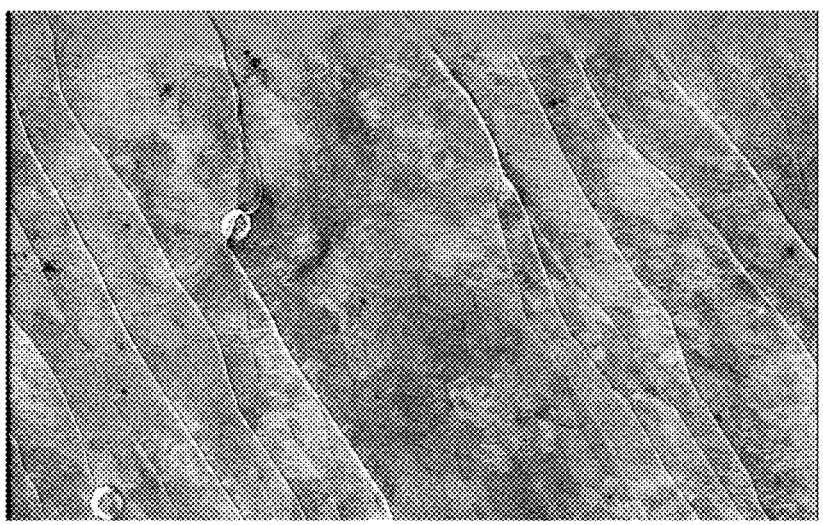
FIGS. 9A-9C show striped chemical templates prepared on graphite (HOPG) typically using device/protocol from PRF No. 67788 and 67869, then transferred to PDMS using the procedure in PRF 68357-01. Templates could also be prepared using device from PRF 68356-01 to achieve even longer-range orders, or through microcontact printing to achieve geometric patterning.
Figure 9B:
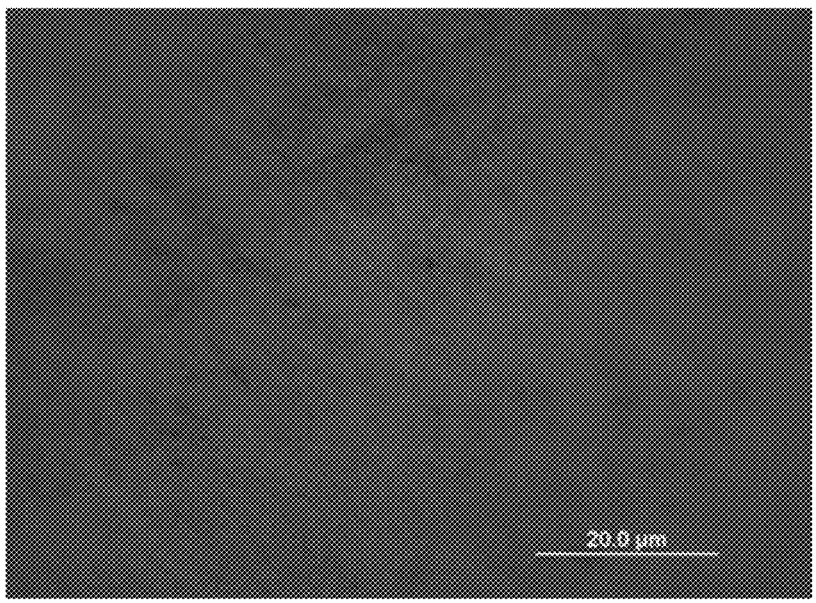
Figure 9C:
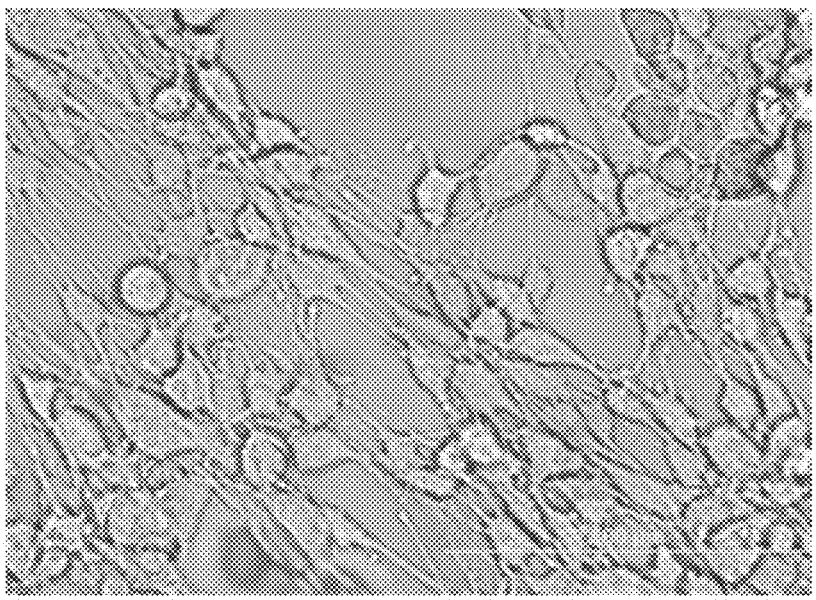
Figures 10A, 10B:
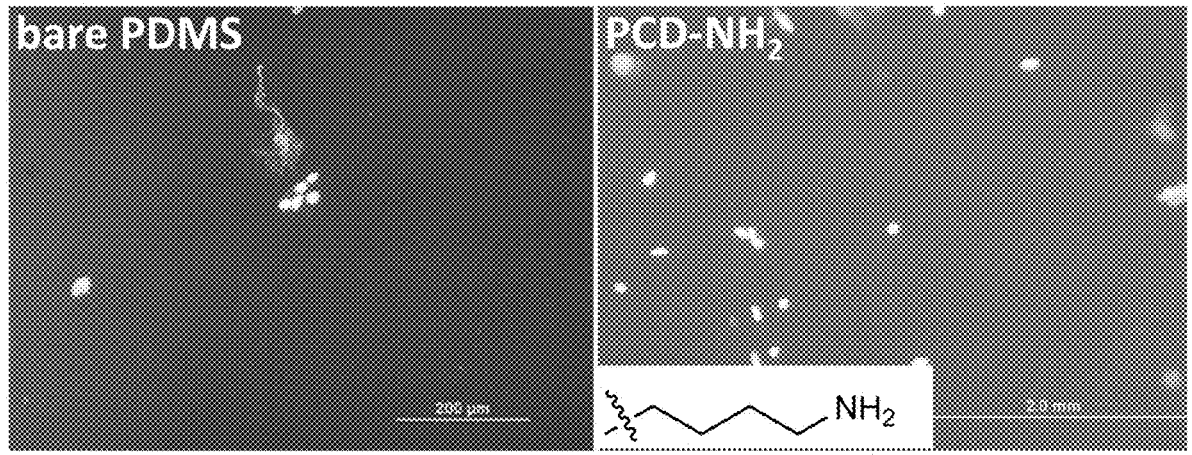
FIGS. 10C-10D show striped phases of phospholipids transferred to PDMS substantially improve cell adhesion and spreading in comparison with bare PDMS (FIG. 10A) and simple amine headgroup (FIG. 10B).
Figures 10C, 10D:
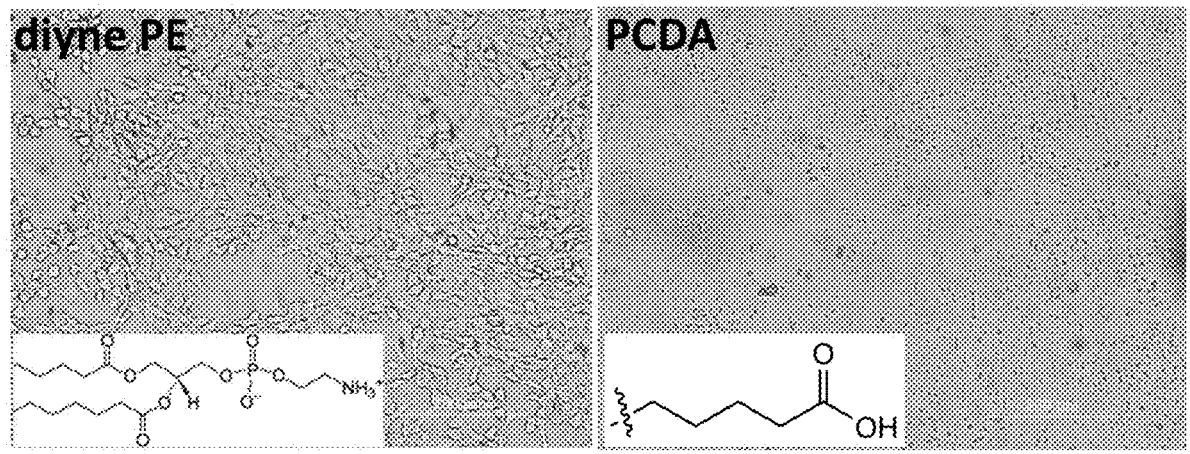
Figures 11A, 11B, 11C:
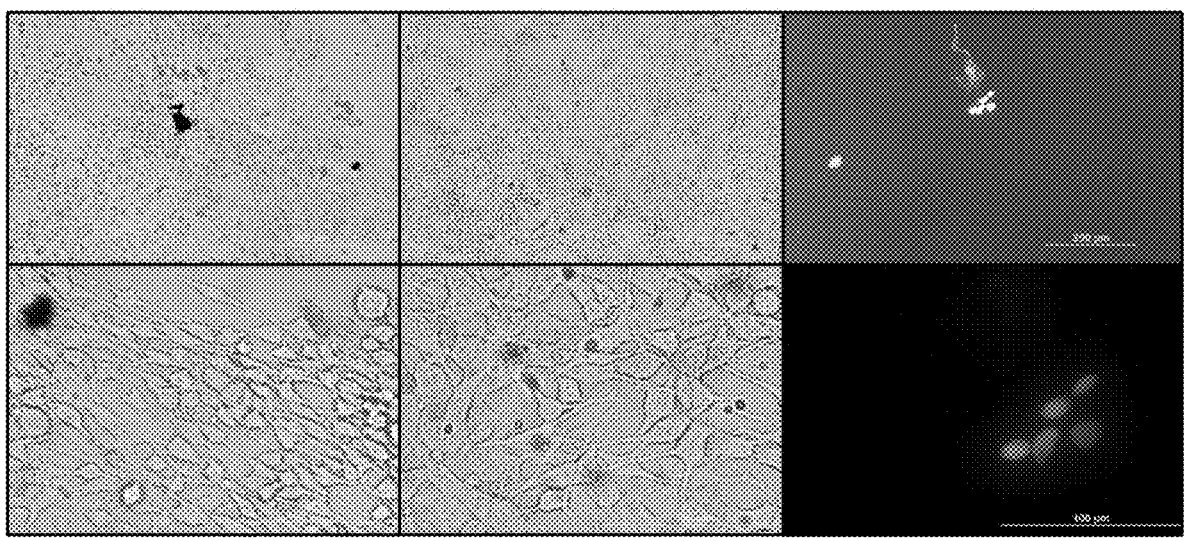
FIGS. 11A-11C show long range ordering in striped template directs cell growth.

Here, our results (FIG. 7) illustrate that C2C12 cells adhere to and spread more extensively on diyne PE-functionalized PDMS surfaces that exhibit relatively long-range order (FIG. 7, top image, cluster lengths 1-10 μm) in comparison with a similar surface exhibiting shorter-range order (cluster lengths ~100 nm). In the top image of FIG. 7, cell growth directions appear to be influenced by the symmetry of the underlying diyne PE striped phase (inset), which can adopt one of three equivalent directionalities when it assembles on the hexagonal HOPG lattice.

Cells exhibit minimal adhesion and spreading on bare PDMS. The bottom images are contrast-enhanced to help visualize spreading.

Cellular interactions with the ECM and other objects in the surroundings are typically mediated though sets of chemical functional groups presented in specific 3D spatial organizations, typically scaffolded on carbohydrates (e.g. hyaluronic acid, HA) or peptides (e.g. integrin binding peptides such as RGD). HA in particular forms an interesting case of functional group clustering in the ECM, since it has molecular weights up to 7 MD (corresponding to stretched polysaccharide lengths up to several μm), and is observed to decrease in molecular weight with aging (decreases from 2 MD to 300 kD reported in by Holmes et al.[9] for human articular cartilage, a length decrease for extended molecules from ~2 μm to ~300 nm).

This platform has the potential to enable researchers to establish the relevance of spatial distributions cell-ECM ligand interactions over scales from molecular to millimeter scales, by either testing against surfaces functionalized with common chemistries or ligands, or by appending specific ligands of interest.

The extracellular matrix has a number of components including collagens, fibronectin, and hyaluronic acid that contribute to its mechanical structure and thus cell adhesion, proliferation, and differentiation. Here, we design a surface that is intended to mimic properties of large polysaccharides including hyaluronic acid. Hyaluronic acid is comprised of a repeating pattern of disaccharides, D-glucuronic acid and N-acetyl-D-glucosamine, linked through β-(1→4) and β-(1→3) glycosidic bonds. The polysaccharides can be exceptionally long (potentially tens of thousands of disaccharide repeat units in length), with spatial extents exceeding 10 micrometers for an individual polysaccharide. Polysaccharide length can vary between tissues, and with conditions including aging; thus, fabricating materials and interfaces capable of mimicking specific physicochemical aspects of these large molecules is of potential importance in materials that direct cell growth, among other applications.

Figure 12A:
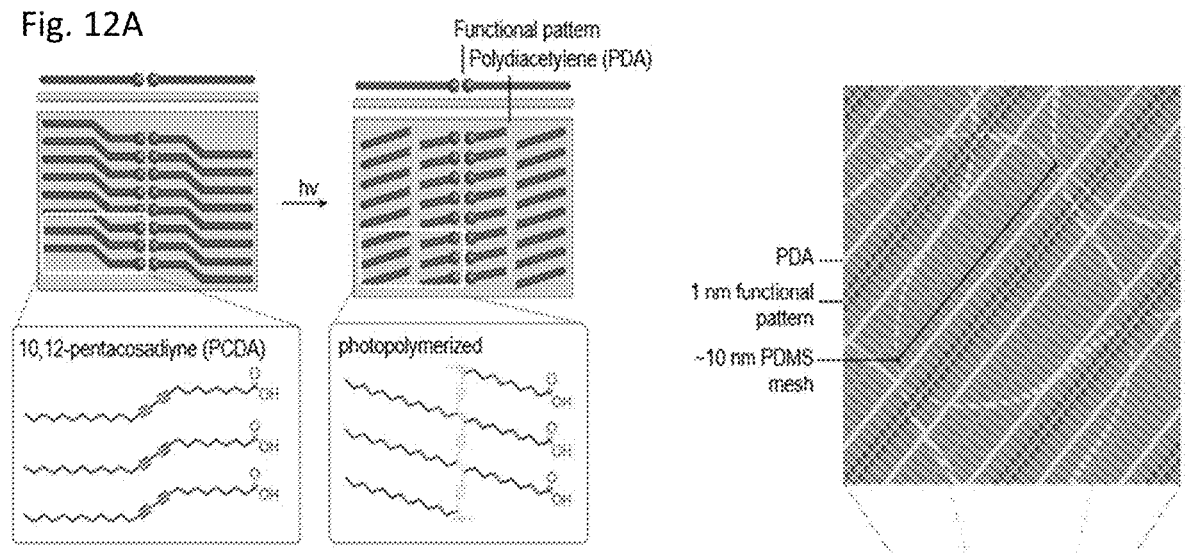
FIG. 12A-12C show process for generating surfaces that mimic specific properties of large polysaccharides such as hyaluronic acid.
Figure 12B:
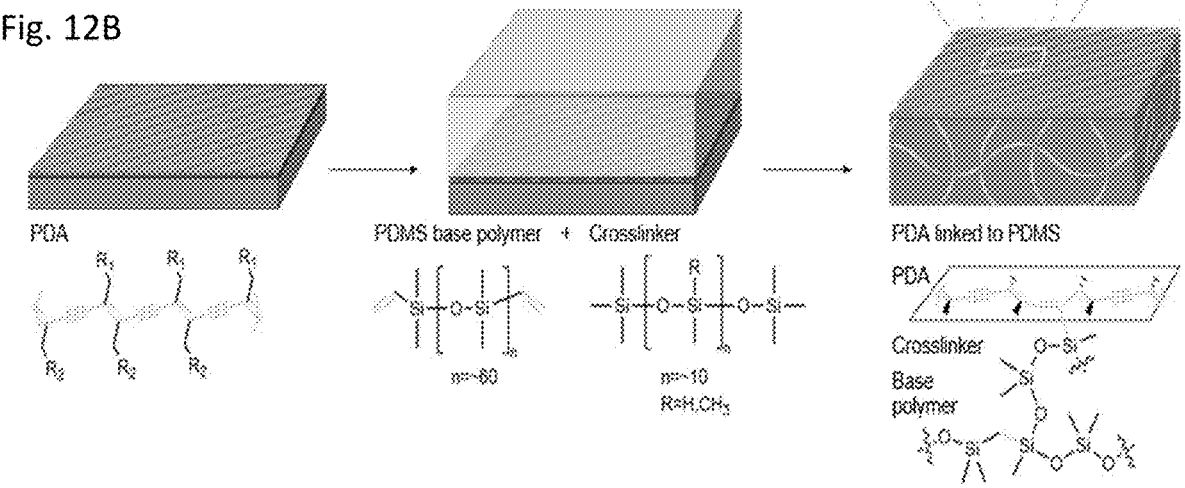
Figure 12C:
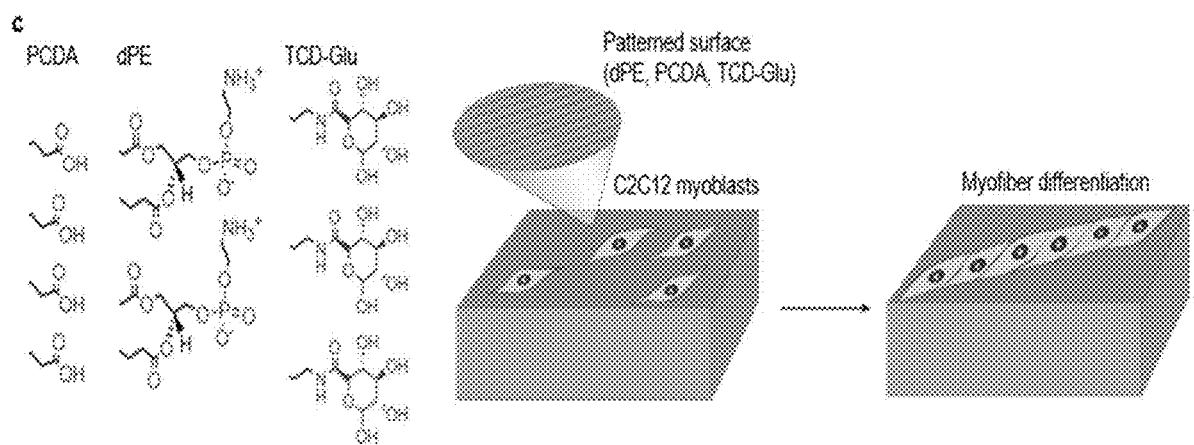

We have prototyped a strategy (see FIG. 12) for making surfaces that mimic specific properties of large polysaccharides such as hyaluronic acid, by:

Preparing a modified amphiphile with carbohydrate headgroup similar to one of the constituents of hyaluronic acid, and an alkyl chain modified with an internal diyne;

Assembling the modified amphiphile on HOPG to achieve a striped phase, in which the molecules lie down on the surface, and the carbohydrate-modified headgroups are aligned over a desired distance;

Photopolymerization of the striped phase to generate carbohydrate polymers with desired lengths; and Optionally, covalent transfer of the amphiphilic carbohydrate polymer layer to a desired substrate (here, PDMS, which is suitable for cell culture).

Figure 13:
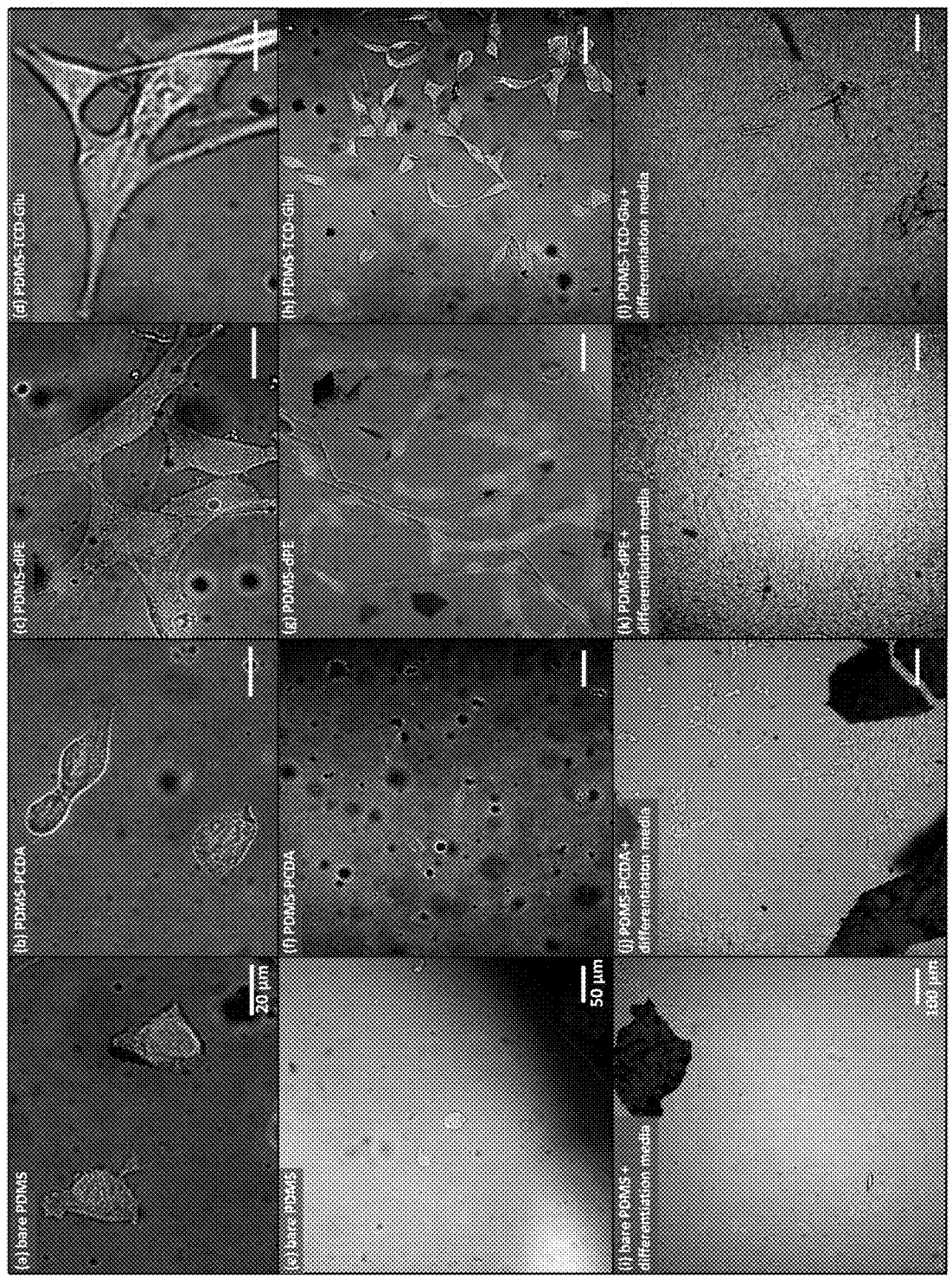
FIG. 13 shows C2C12 murine myoblasts (a cell line commonly used to examine cellular response to surface chemical and topographic cues) cultured on bare PDMS (left column) exhibit very limited adhesion to bare PDMS. Surfaces modified with the amphiphile with a carboxylic acid headgroup (PCDA) also produce fairly limited adhesion (left center column). In contrast, both the zwitterionic phospholipid headgroups (dPE, right center column) and the carbohydrate-modified headgroup (TCD-Glu, right column) produce more extensive adhesion. TCD-Glu also results in modulated cell growth patterns (e.g. curvature) in comparison with dPE. While both dPE and TCD-Glu-modified substrates support myoblast differentiation to form myotubes (bottom row), differentiation is more extensive for the TCD-Glu substrates in comparison with dPE.

We demonstrate that surfaces modified with amphiphilic carbohydrate polymers induce differences in cell adhesion and spreading in comparison with bare PDMS, or amphiphiles which are not modified with the carbohydrate headgroup. In FIG. 13, C2C12 murine myoblasts (a cell line commonly used to examine cellular response to surface chemical and topographic cues) cultured on bare PDMS (left column) exhibit very limited adhesion. Surfaces modified with the amphiphile with a carboxylic acid headgroup (PCDA) also produce fairly limited adhesion (left center column). In contrast, both the zwitterionic phospholipid headgroups (dPE, right center column) and the carbohydrate-modified headgroup (TCD-Glu, right column) produce more extensive adhesion. TCD-Glu also results in modulated cell growth patterns (e.g. curvature) in comparison with dPE. While both dPE and TCD-Glu-modified substrates support myoblast differentiation to form myotubes (bottom row), differentiation is more extensive for the TCD-Glu substrates in comparison with dPE.

Preparation and transfer of striped monolayers on HOPG. Striped monolayers of 10,12-pentacosadiynoic acid (PCDA), 1,2-bis(10,12-tricosadiynoyl)-sn-glycero-3-phosphoethanolamine (diyne PE), 10,12-pentacosadiynamine (PCD-NH$_2$), and 10,12-tricosadiynglucosamine (TCD-GLU) were prepared via Langmuir-Schaefer (LS) conversion based on procedures reported previously by our group[15-17] and others.[18-20] Monolayers were polymerized via UV irradiation; polydimethylsiloxane (PDMS) was then cast on the monolayers. Procedures are described in more detail in the Experimental Methods section.

Monolayers were characterized by AFM and SEM prior to PDMS transfer to examine nanoscopic lamellar structure and microscale domain structure; images of polymerized PCDA monolayers are shown in FIG. 2a and FIG. 2b. AFM images illustrate striped lamellar pattens in epitaxy with the HOPG lattice, while larger SEM images show domain ordering over μm scales, with domains frequently terminating at step edges in the HOPG (long lines running approximately top to bottom in FIG. 2a). The conjugated ene-yne formed through photopolymerization (FIG. 1a) can fluoresce, but on HOPG this fluorescence is not observed, either due to quenching on the semimetallic HOPG surface or due to formation of the nonfluorescent fully-extended form of the polymer backbone (FIG. 2b, inset).

Figure 3:
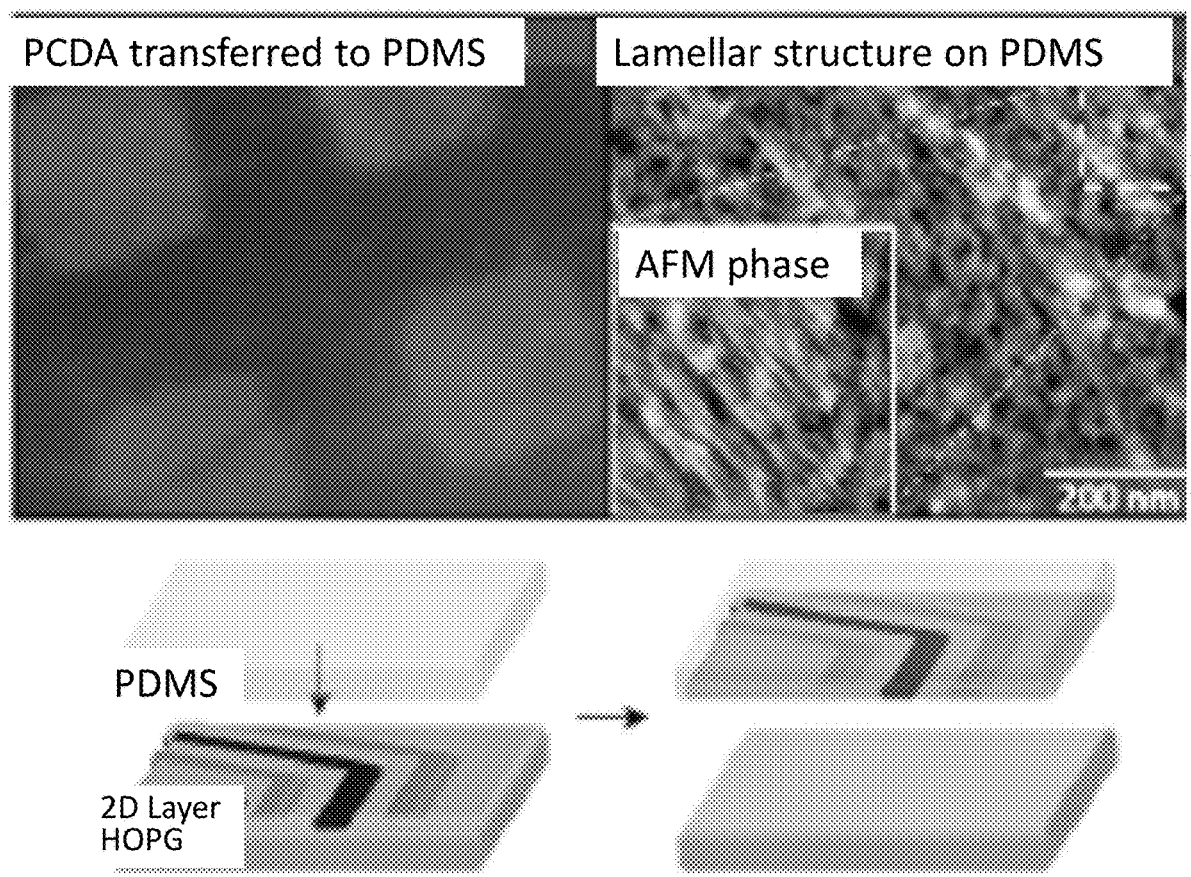
FIG. 3 depicts transfer of ligand cluster patterns to PDMS, providing nanoscale and microscale patterning.
Figure 4:
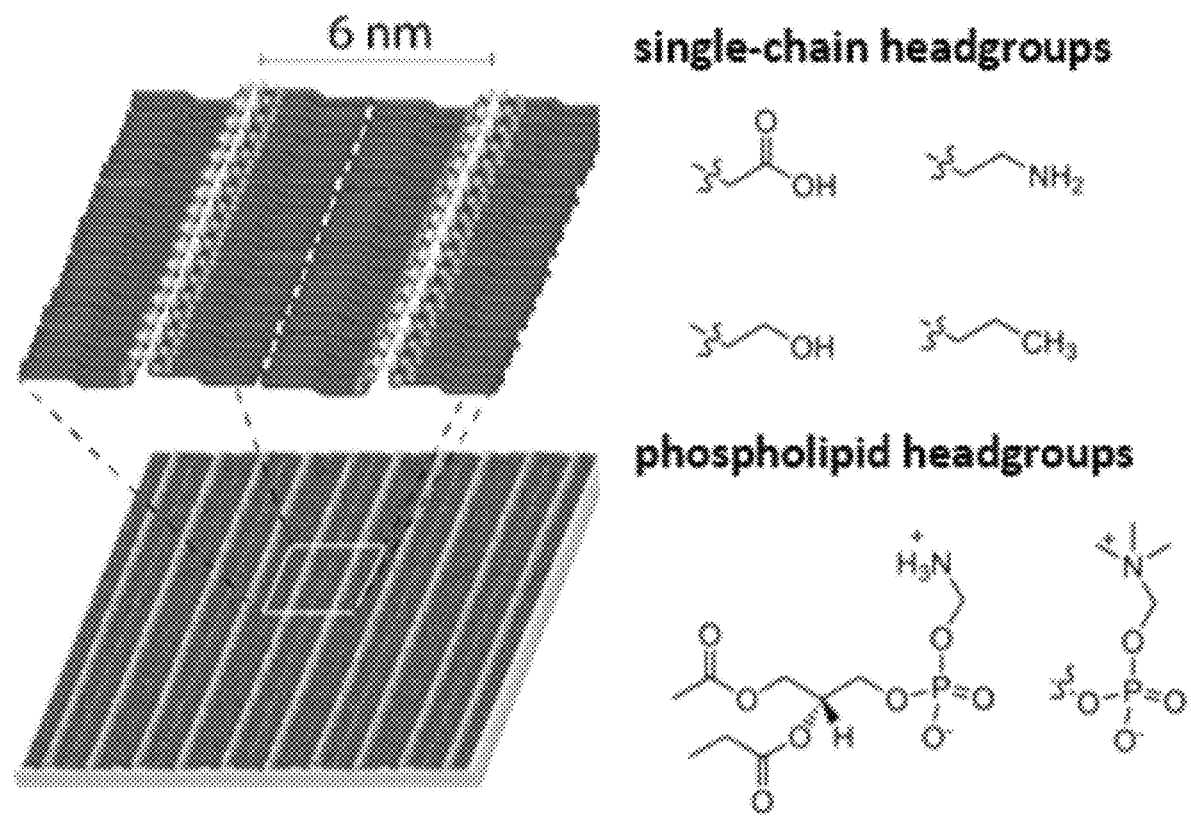
FIG. 4 shows example headgroup (ligand) structures for linear clustering.
Figure 5:
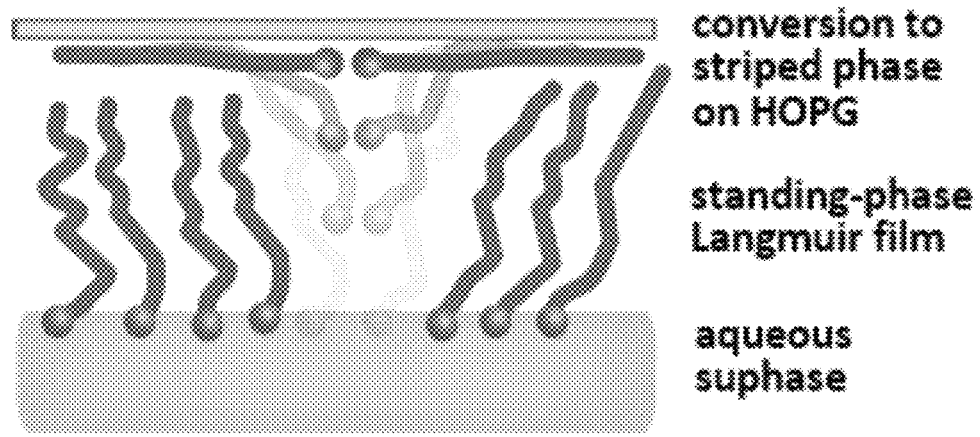
FIG. 5 shows Langmuir-Schaefer conversion of standing-phase Langmuir film to form striped phase on HOPG.
Figure 6:
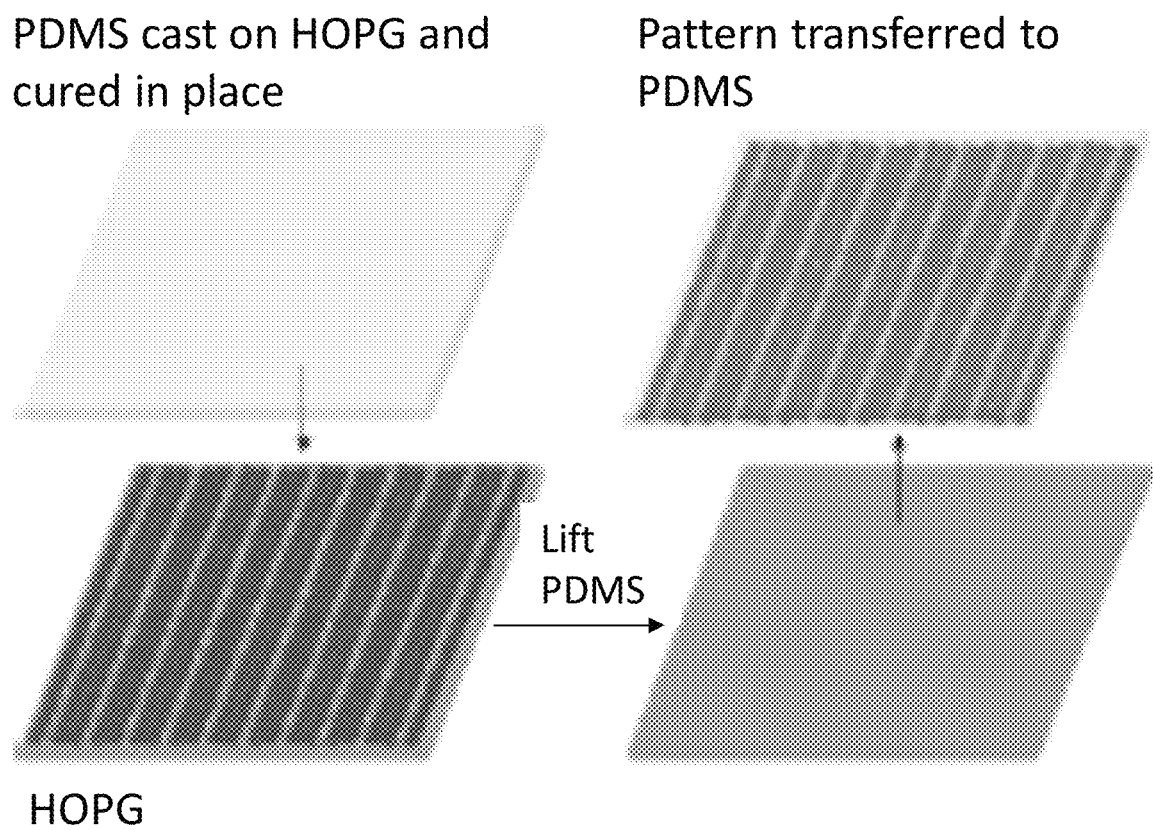
FIG. 6 shows molecular pattern transfer to PDMS.

Comparisons of molecular film structure after transfer to PDMS. After transfer to PDMS, microscopic monolayer structure is visible in both AFM images (FIG. 3a) and fluorescence micrographs (FIG. 3b). AFM images are surface-sensitive; thus, post-transfer surface features with morphologies observed in molecular films on HOPG indicate that the molecular layer remains accessible on the surface, an important criterion for further use. Higher-resolution AFM images (FIG. 3a, inset) reveal nanoscopic vacancies and lamellar orientation. Although the surface appears roughened in comparison with the molecular layer on HOPG, stripe patterns remain visible on the surface, at sub-10-nm periodicities commensurate with PCDA molecular rows.

Optical properties of the ene-yne backbone provide a useful means of characterizing film structure on PDMS. Visible absorption and emission of the conjugated ene-yne have been extensively studied in standing-phase Langmuir films and bulk crystals of PCDA and similar molecules. Quenching of ene-yne fluorescence on HOPG has conventionally precluded optical characterization of such monolayer structures. Here, fluorescence micrographs of PCDA striped phases prior to transfer exhibit minimal emission (FIG. 2b, inset). However, when the film is separated from the HOPG substrate, fluorescence emission from the polymer backbone is observed (FIG. 3b). This capability enables the locations of transferred molecules to be characterized without contacting the surface.

Wetting of molecular film before and after transfer. The ability of a molecular film to control wetting is crucial to its function as an interlayer. Previously, we have found that stripes of functional groups in monolayers on HOPG create substantial changes in wettability, which can depend on relatively small changes in molecular structure.

Functional groups at interfaces often undergo significant changes in their chemical behavior, including their ability to ionize. To assess the chemical behavior of functional groups in the films, we perform contact angle titrations, in which droplets of buffers with pH values ranging from 2-14 are exposed to the films. Ionization of functional groups in the monolayer alters surface hydrophilicity; for instance, ionization of carboxylic acids to carboxylates increases hydrophilicity, resulting in lower contact angles. The midpoint of the sigmoidal decrease in contact angle vs pH is typically taken to be the $pK_{1/2}$, the halfway point in ionization.

Experimental Methods

Procedure for Langmuir-Schaefer (LS) transfer of amphiphile monolayers. LS deposition was performed using a Kibron (Helsinki, Finland) MicroTrough XL. For transfer of single chain amphiphiles, 30 μL of a 0.5 mg/mL solution of the amphiphile in chloroform was deposited onto a subphase of deionized water at 30° C. The trough was equilibrated for 15 min, to allow the solvent from the spreading solution to evaporate; the trough barriers were then slowly swept inwards at a rate of 8.5 mm/min. When the desired packing density condition for transfer was achieved the freshly cleaved HOPG substrate was lowered horizontally into contact with the subphase at a speed of 6 mm/min. After 2 min in contact with the liquid interface, the HOPG was slowly lifted out of contact with the subphase at 6 mm/min.

For phospholipid monolayers, deposition was performed by spreading 30 μL of 0.50 mg/mL solution of diyne PE in chloroform onto a subphase of deionized water at 30° C.

After deposition, the trough was allowed to equilibrate for 15 min, in order to allow the solvent from the spreading solution to evaporate. Transfer was carried out at a surface pressure of 30 mN/m. Freshly cleaved HOPG was heated to 55° C. using a custom built thermally controlled dipping attachment reported previously, then lowered into contact with the subphase at 6 mm/min. The HOPG was left in contact with the interface for 2 min and then withdrawn from the interface using the automated dipper.

All samples were dried with $N_2$ prior to further processing. Diacetylene-functionalized amphiphilic monolayers prepared as described above were then photopolymerized for 1 h via irradiation under a 254-nm 8-W UW lamp with approximately 4 cm between sample and lamp.

PDMS Transfer. SYLGARD 184 silicone elastomer base and curing (crosslinking) agent were mixed at a 10:1 (m/m) ratio. After the components were thoroughly mixed (ca. 5 min), the mixture was poured onto the HOPG substrate functionalized with the diyne amphiphile film. The mixture was then deaerated in a vacuum desiccator until no bubbles remained. The PDMS was cured for 24 h at 60° C. The cured (solid) PDMS was then peeled away from the HOPG substrate, resulting in transfer of the polymerized amphiphile film to the free PDMS.

Cell culture. C2C12 cells were cultured in Advanced DMEM containing 10% FBS, 1× penicillin/streptomycin, and 1% glutagro supplement at 37° C. in 5% $CO_2$. Cells were seeded on sterilized PDMS at $2.5 \times 10^4$ cells/mL and grown to 70% confluence before switching to a 2% horse serum differentiation media. To analyze cell adhesion, spreading, and differentiation, cells were fixed and stained with DAPI (1:1000) and phalloidin (1:200).

Those skilled in the art will recognize that numerous modifications can be made to the specific implementations described above. The implementations should not be limited to the particular limitations described. Other implementations may be possible.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES

1. Plow, E. F.; Haas, T. A.; Zhang, L.; Loftus, J.; Smith, J. W., Ligand Binding to Integrins. *J. Biol. Chem.* 2000, 275, 21785-21788.
2. Stevens, M. M.; George, J. H., Exploring and Engineering the Cell Surface Interface. *Science* 2005, 310, 1135-1138.
3. Love, J. C.; Estroff, L. A.; Kriebel, J. K.; Nuzzo, R. G.; Whitesides, G. M., Self-Assembled Monolayers of Thiolates on Metals as a Form of Nanotechnology. *Chem. Rev.* 2005, 105, 1103-1169.
4. Sackmann, E., Supported Membranes: Scientific and Practical Applications. *Science* 1996, 271, 43-48.
5. Xia, Y. N.; Whitesides, G. M., Soft Lithography. *Annu. Rev. Mater. Sci.* 1998, 28, 153-184.
6. Bang, J. J.; Rupp, K. K.; Russell, S. R.; Choong, S. W.; Claridge, S. A., Sitting Phases of Polymerizable Amphiphiles for Controlled Functionalization of Layered Materials. *J. Am. Chem. Soc.* 2016, 138, 4448-4457.
7. Claridge, S. A., Standing, Lying, and Sitting: Translating Building Principles of the CellMembrane to Synthetic 2D Material Interfaces. *Chem. Comm.* 2018, 54, 6681-6691.
8. Calve, S.; Isaac, J.; Gumucio, J. P.; Mendias, C. L., Hyaluronic Acid, Has1, and Has2 Are Significantly Upregulated During Muscle Hypertrophy. *Am. J. Physiol.—Cell Physiol.* 2012, 303, C577-588.
9. Holmes, M. W. A.; Bayliss, M. T.; Muir, H., Hyaluronic Acid in Human Articular Cartilage. *Biochem. J.* 1988, 250, 435-441.
10. 10. Kalluri, R.; Weinberg, R. A., The Basics of Epithelial-Mesenchymal Transition. *J. Clin. Invest.* 2009, 119, 1420-1428.
11. Lutolf, M. P.; Hubbell, J. A., Synthetic Biomaterials as Instructive Extracellular Microenvironments for Morphogenesis in Tissue Engineering. *Nat. Biotechnol.* 2005, 23, 47-55.
12. Yanagishita, M., Function of Proteoglycans in the Extracellular Matrix. *Acta Pathol. Japon.* 1993, 43, 283-293.
13. Haas, T. A.; Plow, E. F., Integrin-Ligand Interations: A Year in Review. *Curr. Opin. Cell Biol.* 1994, 6, 656-662.
14. Han, X.; Zheng, Y.; Munro, C. J.; Ji, Y.; Braunschweig, A. B., Carbohydrate Nanotechnology: Hierarchical Assembly Using Nature's Other Information Carrying Biopolymers. *Curr. Opin. Biotechnol.* 2015, 34, 41-47.
15. Zhang, S. G.; Yan, L.; Altman, M.; Lassle, M.; Nugent, H.; Frankel, F.; Lauffenburger, D. A.; Whitesides, G. M.; Rich, A., Biological Surface Engineering: A Simple System for Cell Pattern Formation. *Biomater.* 1999, 20, 1213-1220.
16. Hovis, J. S.; Boxer, S. G., Patterning and Composition Arrays of Supported Lipid Bilayers by Microcontact Printing. *Langmuir* 2001, 17, 3400-3405.
17. Kam, L.; Shain, W.; Turner, J. N.; Bizios, R., Axonal Outgrowth of Hippocampal Neurons on Micro-Scale Networks of Polylysine-Conjugated Laminin *Biomater.* 2001, 22, 1049-1054.
18. Arnold, M. S.; Hirschfeld-Warneken, V. C.; Lohmuller, T.; Hell, P.; Blummel, J.; Cavalcanti-Adam, E. A.; Lopez-Garcia, M.; Walther, P.; Kessler, H.; Geiger, B., et al., Induction of Cell Polarization and Migration by a Gradient of Nanoscale Variations in Adhesive Ligand Spacing. *Nano Lett.* 2008, 8, 2063-2069.
19. Buchholz, S.; Rabe, J. P., Molecular Imaging of Alkanol Monolayers on Graphite. *Angew. Chem., Int. Ed. Engl.* 1992, 31, 189-191.
20. De Feyter, S.; De Schryver, F. C., Self-Assembly at the Liquid/Solid Interface: STM Reveals. *J. Phys. Chem. B* 2005, 109, 4290-4302.
21. Okawa, Y.; Aono, M., Materials Science—Nanoscale Control of Chain Polymerization. *Nature* 2001, 409, 683-684.
22. Okawa, Y.; Akai-Kasaya, M.; Kuwahara, Y.; Mandal, S. K.; Aono, M., Controlled Chain Polymerisation and Chemical Soldering for Single-Molecule Electronics. *Nanoscale* 2012, 4, 3013-3028.
23. Villarreal, T. A.; Russell, S. R.; Bang, J. J.; Patterson, J. K.; Claridge, S. A., Modulating Wettability of Layered Materials by Controlling Ligand Polar Headgroup Dynamics. *J. Am. Chem. Soc.* 2017, 139, 11973-11979.
24. Hayes, T. R.; Bang, J. J.; Davis, T. C.; Peterson, C. F.; McMillan, D. G.; Claridge, S. A., Multimicrometer Noncovalent Monolayer Domains on Layered Materials through Thermally Controlled Langmuir-Schaefer Conversion for Noncovalent 2D Functionalization. *ACS Appl. Mater. Interf.* 2017, 9, 36409-36416.

25. Davis, T. C.; Bang, J. J.; Brooks, J. T.; McMillan, D. G.; Claridge, S. A., Hierarchically Patterned Noncovalent Functionalization of 2D Materials by Controlled Langmuir-Schaefer Conversion. *Langmuir* 2018, 34, 1353-1362.
26. Bang, J. J.; Porter, A. G.; Davis, T. C.; Hayes, T. R.; Claridge, S. A., Spatially Controlled Noncovalent Functionalization of 2D Materials Based on Molecular Architecture *Langmuir* 2018, 34, 5454-5463.
27. Porter, A. G.; Ouyang, T.; Hayes, T. R.; Biechele-Speziale, J.; Russell, S. R.; Claridge, S. A., 1-nm-Wide Hydrated Dipole Arrays Regulate AuNW Assembly on Striped Monolayers in Nonpolar Solvent. *In review* 2019.
28. Hayes, T. R.; Bang, J. J.; Davis, T. C.; Peterson, C. F.; McMillan, D. G.; Claridge, S. A., Multimicrometer Noncovalent Monolayer Domains on Layered Materials through Thermally Controlled Langmuir-Schaefer Conversion for Noncovalent 2D Functionalization. *ACS Appl. Mater. Interf* 2017, 9, 36409-36416.
29. Davis, T. C.; Bang, J. J.; Brooks, J. T.; McMillan, D. G.; Claridge, S. A., Hierarchical Noncovalent Functionalization of 2D Materials by Controlled Langmuir-Schaefer Conversion. *Langmuir* 2018, 34, 1353-1362.
30. Gildersleeve, J. C.; Oyindasola, O.; Simpson, J. T.; Allred, B., Improved Procedure for Direct Coupling of Carbohydrates to Proteins Via Reductive Amination. *Bioconj. Chem.* 2008, 19, 1485-1490.

We claim:

1. A surface-functionalized cell culture support, wherein the surface of the support material is modified by a transferred monolayer of polymerized striped phases of molecules comprising one or more chemical functional groups, one or more long alkyl chains, and one or more polymerizable functional groups; wherein said transferred striped monolayer is useful for modulating directional adhesion, proliferation, differentiation, or reprogramming of a cell wherein the spatially controlled arrangement of chemical functional groups of the striped phase occurs at a sub-10-nm scale for the spatial placement of those functional elements, wherein the spatial arrangement of the chemical functional groups of the striped monolayer mimic properties of polysaccharide components of an extracellular matrix useful for modulating adhesion, proliferation, differentiation, or reprogramming of a cell and wherein said chemical functional groups comprise a carbohydrate, Arg-Gly-Asp peptide or a functional analog thereof, a matrisome component, or a combination thereof.

2. The surface-functionalized cell culture support according to claim 1, wherein the spatial arrangement and/or orientation and mechanical coupling of chemical functional groups in the striped phase through the polymerized striped phase polymer backbone mimics signaling and structural elements of macromolecular components of extracellular matrix or matrisome, and therefore modulates the directional adhesion, proliferation, differentiation, or reprogramming of a cell.

3. The surface-functionalized cell culture support according to claim 1, wherein distinct mechanical properties of said cell culture support and said striped phase polymer backbone and/or covalent linkages between the cell culture support and the striped phase polymer backbone participate in modulating the directional adhesion, proliferation, differentiation, or reprogramming of a cell.

4. The surface-functionalized cell culture support according to claim 1, wherein the polysaccharide is hyaluronic acid.

5. The surface-functionalized cell culture support according to claim 1, wherein said cell is a myoblast.

6. The surface-functionalized cell culture support according to claim 1, wherein the support material is polydimethylsiloxane (PDMS).

7. A transferred striped monolayer compatible to be added to a traditional cell culture support comprising polymerized striped phases of molecules comprising one or more chemical functional groups, one or more long alkyl chains, and one or more polymerizable functional groups, wherein said transferred striped monolayer is useful for modulating directional adhesion, proliferation, differentiation, or reprogramming of a cell wherein the striped phases of molecules occurs at a sub-10-nm scale for the spatial placement of those functional elements, wherein the spatial arrangement of the chemical functional groups of the striped monolayer mimic properties of polysaccharide components of an extracellular matrix useful for modulating adhesion, proliferation, differentiation, or reprogramming of a cell and wherein said chemical functional groups comprise a carbohydrate, Arg-Gly-Asp peptide or a functional analog thereof, a matrisome component, or a combination thereof.

8. The transferred striped monolayer compatible to be added to a traditional cell culture support according to claim 7, wherein said traditional cell culture support is polydimethylsiloxane (PDMS).

9. The transferred striped monolayer compatible to be added to a traditional cell culture support according to claim 7, wherein the mechanical coupling of chemical functional groups in the striped phase through the polymerized striped phase polymer backbone modulates the directional adhesion, proliferation, differentiation, or reprogramming of a cell.

10. The transferred striped monolayer compatible to be added to a traditional cell culture support according to claim 7, wherein said cell is used for tissue engineering or repairment.

11. The transferred striped monolayer compatible to be added to a traditional cell culture support according to claim 7, wherein said cell is a myoblast.

12. The transferred striped monolayer compatible to be added to a traditional cell culture support according to claim 7, wherein the spatial arrangement and/or orientation and mechanical coupling of chemical functional groups in the striped phase through the polymerized striped phase polymer backbone mimics signaling and structural elements of macromolecular components of extracellular matrix or matrisome, and therefore modulates the directional adhesion, proliferation, differentiation, or reprogramming of a cell.

13. The transferred striped monolayer compatible to be added to a traditional cell culture support according to claim 7, wherein distinct mechanical properties of said cell culture support and said striped phase polymer backbone and/or covalent linkages between the cell culture support and the polymer backbone participate in modulating the directional adhesion, proliferation, differentiation, or reprogramming of a cell.

14. A surface or a template comprising a monolayer of a polymerized striped phase with chemical functional groups, wherein the structure of said striped phase spatially controls arrangement of said functional groups with elements of the spatial placement occurring at sub-10-nm scales, and wherein said striped monolayer mimics properties of macromolecules or components of the extracellular matrix useful for modulating the directional adhesion, proliferation, differentiation, or reprogramming of a cell wherein the spatially controlled arrangement of chemical functional groups in the striped phase with elements of the spatial placement occurs at a sub-10-nm scale wherein said chemical functional groups comprise a carbohydrate, Arg-Gly-Asp peptide or a functional analog thereof, a matrisome component, or a combination thereof.

15. The surface or template according to claim 14, wherein the arrangement of the chemical functional groups of the striped monolayer mimic properties of polysaccharide components of an extracellular matrix useful for modulating adhesion, proliferation, differentiation, or reprogramming of a cell.

16. A method for organizing or directing cell growth, or for tissue engineering, wherein said method utilizes the surface or template according to claim 14.

* * * * *